(12) United States Patent
Irion et al.

(10) Patent No.: US 8,187,171 B2
(45) Date of Patent: May 29, 2012

(54) VIDEO ENDOSCOPE

(75) Inventors: Klaus M. Irion, Emmingen-Liptingen (DE); Peter Schwarz, Tuttlingen (DE); Christian Graf, Emmingen-Liptingen (DE); Frank Rockenstiehl, Balingen (DE)

(73) Assignee: Karl Storz GmbH & Co. KG (DE)

( * ) Notice: Subject to any disclaimer, the term of this patent is extended or adjusted under 35 U.S.C. 154(b) by 1141 days.

(21) Appl. No.: 12/031,345

(22) Filed: Feb. 14, 2008

(65) Prior Publication Data
US 2008/0214892 A1 Sep. 4, 2008

(30) Foreign Application Priority Data
Feb. 16, 2007 (DE) .......................... 10 2007 009 292

(51) Int. Cl.
*A61B 1/005* (2006.01)
*A61B 1/05* (2006.01)
(52) U.S. Cl. ......... 600/110; 600/173; 600/137; 600/130
(58) Field of Classification Search .................. 600/110, 600/112, 109, 104, 424, 102, 173, 130, 137; 348/373, 376, 65, 76
See application file for complete search history.

(56) References Cited

U.S. PATENT DOCUMENTS

| | | | |
|---|---|---|---|
| 4,858,001 A | 8/1989 | Milbank et al. | |
| 5,313,306 A | 5/1994 | Kuban et al. | |
| 5,621,830 A * | 4/1997 | Lucey et al. | 385/25 |
| 6,097,423 A * | 8/2000 | Mattsson-Boze et al. | 348/65 |
| 6,293,910 B1 * | 9/2001 | Yamakita et al. | 600/132 |
| 6,464,631 B1 | 10/2002 | Girke et al. | |
| 6,471,637 B1 * | 10/2002 | Green et al. | 600/109 |
| 6,488,631 B2 | 12/2002 | Ohara et al. | |
| 7,108,657 B2 * | 9/2006 | Irion et al. | 600/110 |
| 7,713,189 B2 * | 5/2010 | Hanke | 600/109 |
| 2002/0062083 A1 | 5/2002 | Ohara et al. | |
| 2002/0161280 A1 * | 10/2002 | Chatenever et al. | 600/112 |
| 2004/0171912 A1 | 9/2004 | Shimizu | |
| 2005/0174479 A1 * | 8/2005 | Kosako | 348/376 |
| 2005/0197533 A1 * | 9/2005 | May et al. | 600/164 |
| 2006/0058581 A1 | 3/2006 | Hanke | |

(Continued)

FOREIGN PATENT DOCUMENTS
DE 201 13 031 12/2001
(Continued)

OTHER PUBLICATIONS
European Search Report, EP08001973, Aug. 14, 2008, 6 Pages.

*Primary Examiner* — John P Leubecker
*Assistant Examiner* — Ronald D Colque
(74) *Attorney, Agent, or Firm* — St. Onge Steward Johnston & Reens LLC

(57) ABSTRACT

A video endoscope comprises an elongate shaft having a longitudinal axis, and a handpiece at the proximal end of the shaft, a distal end of the shaft being provided with a lens and, in the proximal direction from the lens, with an electronic image pickup. The image pickup is connected, via an electrical connection extending along the shaft, to an electrical connector piece arranged on the handpiece. The image pickup and the connector piece can rotate relative to each other about the longitudinal axis of the shaft. The electrical connection comprises at least one flexible, elongate circuit board, which is able to twist about its longitudinal direction and has at least one conductor track.

23 Claims, 9 Drawing Sheets

U.S. PATENT DOCUMENTS

| | | | |
|---|---|---|---|
| 2006/0129032 A1* | 6/2006 | Durell | 600/173 |
| 2008/0108869 A1* | 5/2008 | Sanders et al. | 600/109 |

FOREIGN PATENT DOCUMENTS

| | | |
|---|---|---|
| DE | 10 2004 023 866 | 2/2006 |
| DE | 10 2004 044 119 | 3/2006 |
| EP | 7 12 289 | 5/1996 |
| EP | 0904725 A1 | 3/1999 |
| FR | 2800983 A1 | 5/2001 |
| WO | 95/01749 | 1/1995 |
| WO | 02102224 A2 | 12/2002 |

* cited by examiner

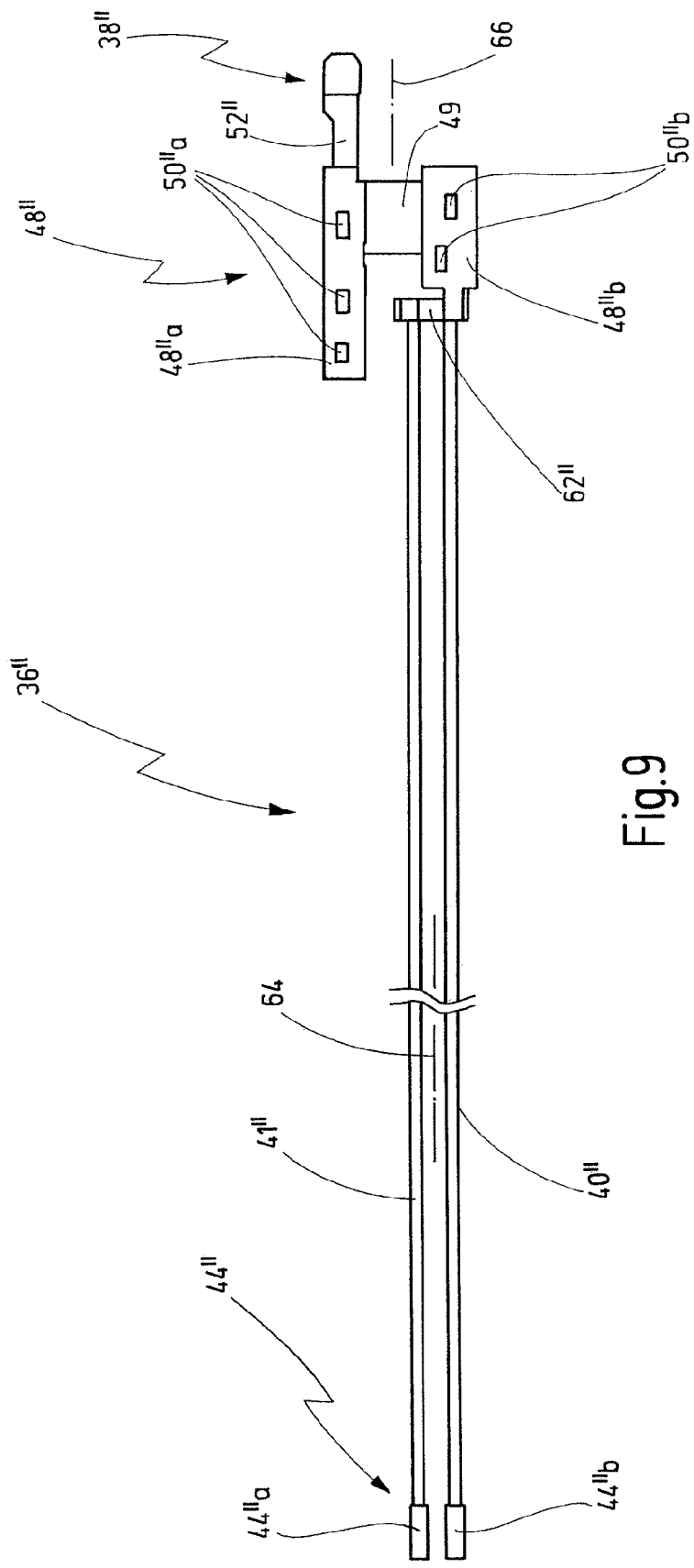

VIDEO ENDOSCOPE

CROSS REFERENCE TO RELATED APPLICATION

The present application claims priority of German patent application no. 10 2007 009 292.1 filed on Feb. 16, 2007.

BACKGROUND OF THE INVENTION

The invention relates to a video endoscope, comprising an elongate shaft having a longitudinal axis, and a handpiece at the proximal end of the shaft, a distal end of the shaft being provided with a lens and, in the proximal direction from the lens, with an electronic image pickup, the image pickup being connected, via an electrical connection extending along the shaft, to an electrical connector piece arranged in the area of the handpiece, and the image pickup and the connector piece being able to rotate relative to each other about the longitudinal axis of the shaft.

A video endoscope is a viewing instrument used in medical endoscopy. Use of a video endoscope in the field of minimally invasive surgery allows regions of the body to be reached by way of natural openings in the body and also by way of artificial incisions that have been created surgically. In endoscopes in general, a distinction is made between those with a rigid elongate shaft and those with a flexible elongate shaft. The present invention can be applied to both rigid video endoscopes and flexible video endoscopes.

A video endoscope is a special type of endoscope in which the images are picked up and conveyed not by a lens system or an organized bundle of optical fibres, but instead by an electronic image pickup and electrical leads.

Since miniaturized electronic image pickups are presently available, for example in CCD or CMOS technology, it is possible to arrange the electronic image pickup in the distal end of the shaft. The object being viewed is projected onto the image pickup via a lens arranged in the distal direction from the electronic image pickup. The electronic image pickup converts the received photons into electrical signals, which are carried in the proximal direction to an electrical connector piece by way of one or more electrical leads that extend from the image pickup all the way through the shaft to the handpiece of the video endoscope. By way of the electrical connector piece, the video endoscope is connected by means of a cable to an image-processing unit that includes a monitor, and the image recorded by the image pickup is displayed on the monitor. The electrical connection extending through the shaft is also used to control and supply power to the distal image pickup.

In video endoscopes with a distal electronic image pickup, the orientation of the physician relative to the video image displayed on the screen is made difficult if the video endoscope is rotated about its longitudinal axis during viewing of a region of the body. If the image pickup is fixed in terms of rotation relative to the shaft, the image pickup is also rotated about its longitudinal axis along with the rotation of the video endoscope, which necessarily causes rotation of the image on the monitor.

In video endoscopes in which the lens has a straight view optic or so-called 0° optic, this problem of orientation can be overcome by means of markings on the handgrip and in the monitor image.

However, this problem is more serious in video endoscopes in which the lens has an oblique optic, for example a 30°, 45° or 90° optic. When a video endoscope with an oblique optic is rotated about its longitudinal axis, the viewing direction changes, as also does the orientation of the viewed image, with respect to top, bottom, right and left. Even with markings on the handgrip of the video endoscope and in the monitor image, the physician is unable to reliably orient himself spatially in the observed region of the body.

For this reason, concepts were proposed in which the image on the monitor can be corrected in orientation, such that the image on the monitor at all times has a defined orientation with respect to top, bottom, right and left.

One of these concepts involves rotating the monitor itself. Although rotation of the monitor is possible, it requires complex electromechanical attachments, which in the operating environment are to be seen as critical. In addition, the usual 4:3 or 16:9 (HDTV) image size is not especially suitable for a mechanical or even an analogue electronic rotation, as is described in EP 712 289 A1.

Another concept is for the image shown on the monitor to be rotated by means of image processing, such as is described in U.S. Pat. No. 5,313,306, for example. However, image correction by means of digital image processing has the disadvantage that no full-format 4:3 image can be rotated without loss of information. Only the inscribed circle in the 3:3 square can be rotated without loss of information. However, the physicians working with video endoscopes are familiar with full-format images, especially in laparoscopy (surgery of the abdominal cavity), and with corresponding full-format image information and do not want to do without these.

The third concept of image correction, from which the present invention starts out, involves making the electronic image pickup rotatable. When the video endoscope is rotated about its longitudinal axis, the image pickup, in order to maintain a defined orientation, can be kept spatially fixed by rotation relative to the shaft and relative to the lens fixed to the shaft. The image pickup is thereby not coupled to the lens, which is of advantage especially in the case of an oblique view lens.

However, the rotatability of the image pickup relative to the shaft and thus also to the proximal electrical connector piece imposes other demands on the video endoscope, particularly on the electrical connection between the image pickup and the proximal electrical connector piece.

Upon rotation of the image pickup relative to the shaft, the at least one electrical connection between the image pickup and the electrical connector piece is necessarily rotated if the electrical connector piece at the proximal end of the handpiece is fixed in terms of rotation with respect to the shaft.

In the document DE 201 13 031 U1, the electrical connection between the image pickup and the electrical connector piece is formed by a multicore cable. Since the rotatability of the image pickup in a video endoscope with an oblique view optic should be possible both clockwise and anticlockwise through 180°, the multicore cable is correspondingly subjected to considerable torsion. After a certain number of changes of load and/or after several sterilizations in an autoclave, the cable has a tendency to break, which has the disadvantage of shortening the useful life of the video endoscope.

To solve this problem, DE 201 13 031 U1 proposes that a sliding contact be provided at the proximal end of the cable, such that the cable, together with the image pickup, can be rotated in a manner free of torsion about its longitudinal axis relative to the electrical connector piece. However, this solution has the disadvantage that it is structurally very complicated and is also susceptible to malfunction.

Another disadvantage of designing the electrical connection as a multicore cable is the great complexity of producing the video endoscope, because each core has to be individually connected to the image pickup, which is very difficult, particularly in a miniaturized configuration of the image pickup.

U.S. Pat. No. 6,488,631 B2 discloses an ultrasound endoscope in which the electrical connection between distally arranged ultrasound transducers and proximal connector piece is formed, in the area of a distal bend of the endoscope, by a multiplicity of flexible circuit boards, which are cut from a tube. The electronic image pickup of this endoscope, by contrast, is electrically connected to the proximal connector piece by means of a multicore cable.

SUMMARY OF THE INVENTION

The object of the invention is to develop a video endoscope of the type mentioned at the outset in such a way that the electrical connection between the image pickup and the electrical connector piece is designed with minimal complexity and therefore inexpensively and is also secure against fatigue, thus increasing the useful life of the video endoscope.

According to the invention, a video endoscope is provided, comprising an elongate shaft having a distal end, a proximal end and a longitudinal axis between the distal end and the proximal end; a handpiece arranged at the proximal end of the shaft; a lens arranged at the distal end of the shaft; an image pickup arranged at the distal end of the shaft proximally from the lens; an electrical connector piece arranged on the handpiece; the image pickup and the electrical connector piece being able to rotate relative to one another about the longitudinal axis of the shaft; and at least one flexible, elongate and narrow circuit board for electrically connecting the image pickup with the electrical connector piece, which extends along the shaft and has a longitudinal direction, the at least one circuit board being able to twist about the longitudinal direction and having at least one conductor track.

In the video endoscope according to the invention, the electrical connection between the image pickup and the proximal electrical connector piece is embodied, not by a multicore cable, but instead by at least one conductor track formed on a flexible, elongate and narrow circuit board. The flexibility of the at least one circuit board ensures that, when the image pickup rotates relative to the electrical connector piece, the circuit board can turn or twist about itself without breaking, even after a large number of alternate rotations, and without the at least one conductor track breaking. The at least one conductor track can be embodied as a very thin metallization on the otherwise insulating circuit board. This at least one conductor track, or even several conductor tracks, can be formed in or near the neutral zone where a twisting of the circuit board causes no or virtually no twisting of the conductor track, as a result of which the conductor track is not substantially compressed or extended.

The use of at least one circuit board as electrical connection between the image pickup and the proximal electrical connector piece also has the advantage that a plurality of conductor tracks in the form of thin metallizations, for example copper, can be applied to a circuit board, as are necessary for contact with the image pickup, for example as in CCD or CMOS chips. The use of a plurality of cables or of a multicore cable is thus advantageously dispensed with.

The circuit board also has the advantage that, at the same time as having a high degree of flexibility, it also has a high degree of mechanical stability, and also temperature stability that can easily withstand the conditions in an autoclave. Forming the electrical connection of the image pickup as at least one circuit board is additionally cost-effective compared to cable systems, because the elongate, flexible circuit board, and also the optionally present circuit board parts still to be described below, can be produced from a single planar material.

The use of at least one circuit board also makes it easier to assemble the video endoscope according to the invention, because instead of several cores having to be individually brought into contact with the image pickup, the contact can be established in a single go, for example using a bar soldering device.

In a preferred embodiment, the at least one circuit board has a plurality of conductor tracks that are arranged next to one another and at most in two planes of the circuit board.

This measure has the advantage that, in a design with a maximum of two layers, the at least one circuit board can be made very thin and the conductor tracks can be arranged in the central zone in which they are neither substantially extended nor substantially compressed by the flexural stress of the at least one circuit board. Since the conductor tracks can be applied linearly onto the circuit board, it is possible for a plurality of conductor tracks to be arranged next to one another on such a circuit board.

In another preferred embodiment, the circuit board is a first circuit board, and the electrical connection comprises a second flexible, elongate and narrow circuit board which is able to twist about its longitudinal direction and has at least one conductor track.

The advantage of this measure is that two flexible elongate circuit boards can together carry more conductor tracks than can one circuit board, and both circuit boards can be made narrow for the purpose of greater flexibility. Narrower circuit boards in turn have the advantage that they are more easily able to twist along the length of the tube of the video endoscope. Because of their narrower configuration, two circuit boards can also be more easily integrated into the shaft of the video endoscope, because they can be arranged with one lying over the other. A further point that should be considered is that electrical image pickups often have two rows of lateral connector pins, such that an electrical connection via two circuit boards is also better adapted mechanically to the conditions of the image pickup.

In this connection, it is preferable if the first and second circuit boards are arranged lying one over the other in the shaft and are movable relative to each other.

This measure has the advantage that the space in the shaft of the video endoscope can be better utilized by the arrangement in which the circuit boards lie one over the other and are accordingly arranged in two planes. The mobility of the two circuit boards relative to each other ensures that the flexibility of such a circuit board arrangement is not reduced by comparison with a single circuit board.

In another preferred embodiment, the second circuit board has a plurality of conductor tracks which are arranged next to one another and in at most two planes of the second circuit board.

Here too, the advantage is once again that single-layer or at most two-layer circuit boards have optimal flexibility and yet sufficient stability.

In another preferred embodiment, the first and second circuit boards are connected to each other in the area of their proximal end via a flexible bridge.

This measure has the advantage that the two circuit boards can be electrically connected to each other via the bridge, which for this purpose has conductor tracks, such that only one of the circuit boards has to be connected to the connector piece.

The flexible bridge is preferably located in the handpiece of the video endoscope and is not subjected there to rotational stress like the circuit boards, which extend all the way through the shaft.

In another preferred embodiment, the at least one circuit board is adjoined proximally by at least one proximal and preferably rigid circuit board part, which carries electrical components.

The advantage of this is that further electronic elements for image pickup control, for example for identification of the image pickup, running time compensation of the video endoscope, adjustment of amplification, can be integrated into the electrical connection. A rigid design of the circuit board part has the advantage that it can be more easily produced with the components.

It is also preferable if the proximal circuit board part is connected by a flexible bridge to another proximal and preferably rigid circuit board part, which carries electrical components.

The advantage of this is that the number of electrical components that can be arranged proximally on the circuit board can be increased, and the two proximal circuit board parts can be electrically connected to each other advantageously via the flexible bridge in the handpiece.

In an advantageously space-saving arrangement, the two proximal circuit board parts are arranged lying one over the other in the handgrip.

In another preferred embodiment, the at least one proximal circuit board part has the electrical connector piece.

The advantage of this is that the electrical connector piece can already be integrated upon production of the whole electrical connection composed of circuit board(s) and proximal circuit board part(s), such that the entire electrical connection can be installed as a prefabricated structural unit into the handpiece and into the shaft, which reduces the production costs of the video endoscope.

In another preferred embodiment, the at least one circuit board has, at its distal end, a distal and preferably rigid circuit board part for contact with the image pickup.

The distal circuit board part serves as interface to the image pickup, the advantage of which is that the contact is easy to produce.

As is provided for in another preferred embodiment, the rigid circuit board part or parts can be produced in one piece with the flexible circuit board from a planar base material. To ensure that the distal circuit board parts are rigid, they can be made from the same base material as the circuit board itself, which is then strengthened in the area of the distal circuit board parts.

In the case of two circuit boards, each with a distal and rigid circuit board part, the two distal circuit board parts can be mechanically and electrically connected, for example by two soldered wires inserted through them, in order to increase the mechanical strength in the area of contact with the image pickup.

In another preferred embodiment, the distal circuit board part is thicker and/or wider than the circuit board adjoining the distal circuit board part.

The flexibility of the electrical connection must be ensured in the section extending substantially through the shaft, that is to say in the area of the flexible circuit board. By contrast, the distal circuit board part is preferably rigid and can therefore also be thicker and/or wider than the part of the circuit board adjoining the distal circuit board part, thus advantageously permitting the additional coverage of the distal circuit board part with electrical components.

It is also preferable if the width of the distal circuit board part and/or the width of the at least one circuit board, in its section extending through the shaft, is at most as great as the width of the image pickup.

The advantage of this is that the at least one circuit board with its rigid and distal circuit board part, or the two circuit boards with their respective distal and rigid circuit board part, can be easily pushed from proximal to distal through the shaft of the video endoscope, after which they can be placed in contact with the image pickup.

In another preferred embodiment, the flexibility of the at least one circuit board decreases continuously or in steps from the proximal end to the distal end, as far as the distal circuit board part.

In this embodiment, the at least one circuit board becomes increasingly more flexible from distal to proximal, which has the advantage that the load occurring upon twisting of the at least one circuit board does not act at the point of transition to the rigid distal circuit board part, but is instead spread proximally over a long area.

In another preferred embodiment, the at least one circuit board is produced in one piece from a planar base material.

The advantage of this is that the circuit board can be produced inexpensively.

In connection with one of the abovementioned embodiments in which two circuit boards are provided and are connected to each other via a flexible bridge, it is also preferable if the first and second circuit boards and the bridge connecting them are made in one piece from a planar base material.

In connection with one of the abovementioned embodiments in which the at least one circuit board has a proximal circuit board part, it is also preferable if the at least one circuit board and the at least one proximal circuit board part are produced in one piece from a planar base material.

If, as in one of the abovementioned embodiments, the at least one circuit board has a distal circuit board part, it is preferable if the at least one circuit board and the at least one distal circuit board part are produced in one piece from a planar base material.

In another preferred embodiment, the aforementioned base material is a polymer, in particular polyimide.

A polymer, in particular polyimide, has the advantage of a high degree of flexibility and inherent rotatability, and also good insulating properties and a low weight. Polyimide has in particular the advantage of very high thermal stability at temperatures of over 200°, which is very advantageous for sterilizing the video endoscope in an autoclave.

As an alternative to the one-piece configuration of the at least one circuit board and/or of the circuit board parts, provision is preferably made for the at least one circuit board to be constructed from a plurality of circuit board sections that have different degrees of flexibility.

For this purpose, sections of the circuit board can be made from differently flexible base materials. Similarly, the aforementioned distal circuit board part and the proximal circuit board part can in particular be designed as rigid plates that are more stable than the circuit board and that are thus better suited for application of electrical components. In particular, with a rigid configuration, the at least one proximal circuit board part can be more easily fitted in the handpiece. Rigid circuit board parts simplify the contact of electrical components and also the contact of the image pickup on the distal circuit board part and of the electrical connector piece on the proximal circuit board part.

In another preferred embodiment, the at least one circuit board is constructed, in its flexible area, from several circuit board layers, preferably from two circuit board layers.

While single-layer circuit boards have the advantage of a very high degree of flexibility, the multi-layer circuit boards, which can also be provided only in sections, have the advantage of allowing complex circuitry to be provided within a very confined space.

Further advantages and features will become evident from the following description and from the attached drawing.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

Illustrative embodiments of the invention are described in more detail below with reference to the drawing, in which:

FIG. 1A shows an enlarged view of a detail of the video endoscope in FIG. 1;

FIG. 9 shows another illustrative embodiment of an electrical connection for the video endoscope in FIG. 1 or in FIG. 5.

DETAILED DESCRIPTION OF PREFERRED EXEMPLARY EMBODIMENTS

A first illustrative embodiment of a video endoscope designated by the general reference number 10 is shown in FIGS. 1 to 4. A detail of the video endoscope 10 is depicted in FIG. 1A.

The video endoscope 10 is used, for example in the context of minimally invasive surgery, for viewing an area of the body inside the body.

Figure 1:
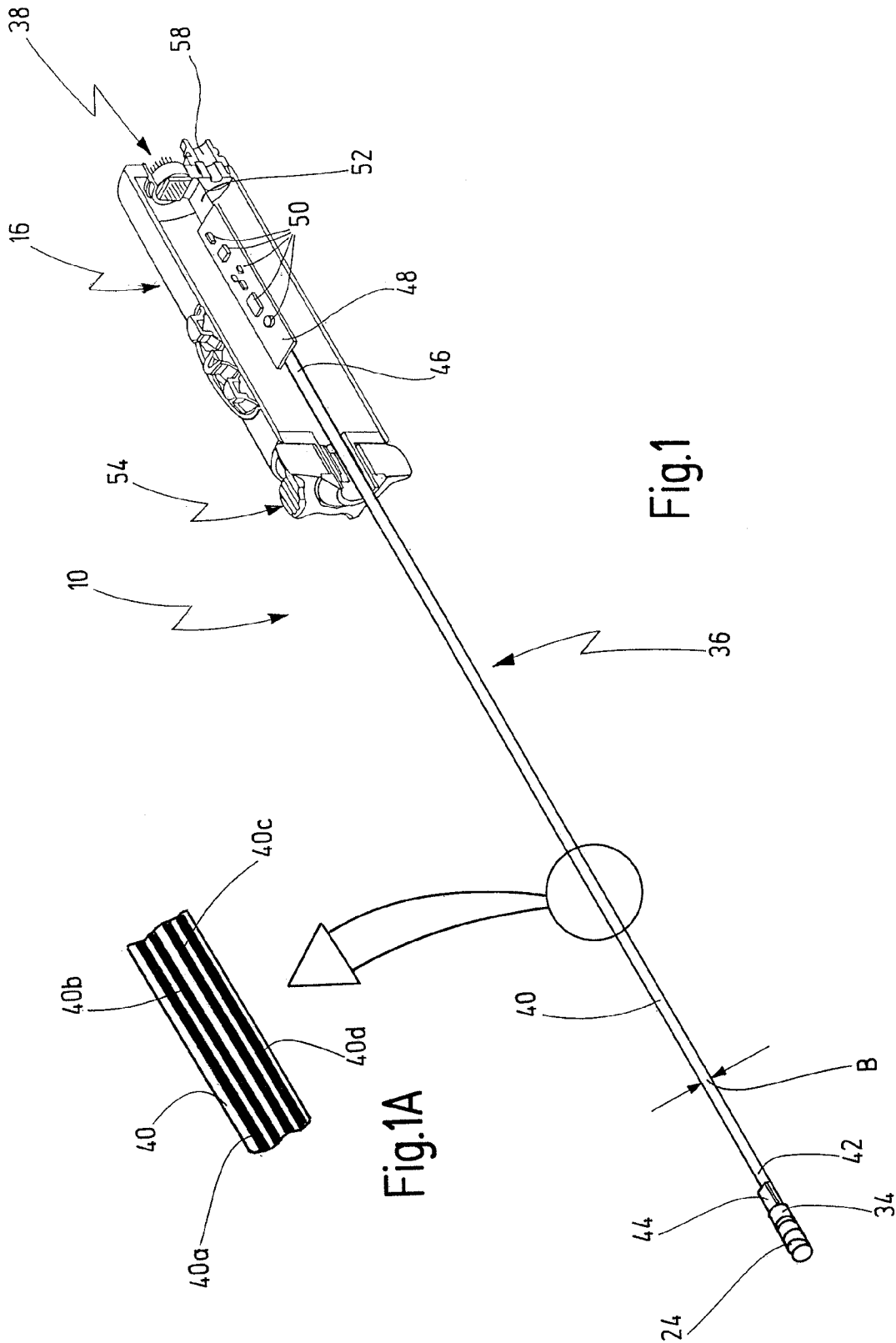
FIG. 1 shows a perspective view of a video endoscope according to a first illustrative embodiment, where parts of the video endoscope have been omitted, and where the video endoscope is depicted partially in longitudinal section.
Figure 2:
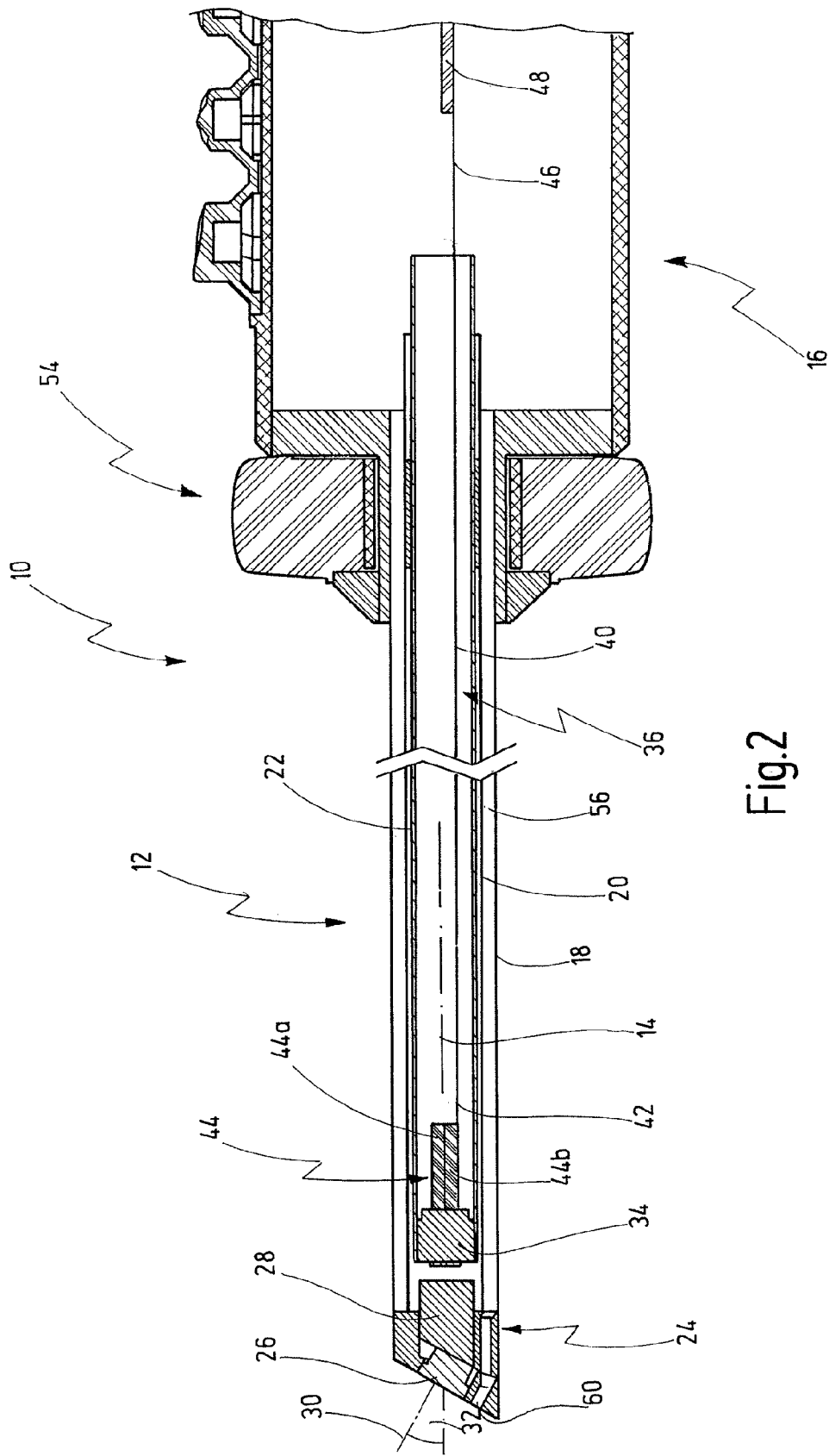
FIG. 2 shows a cutaway view of the video endoscope in FIG. 1, on an enlarged scale and in longitudinal section.
Figure 3:
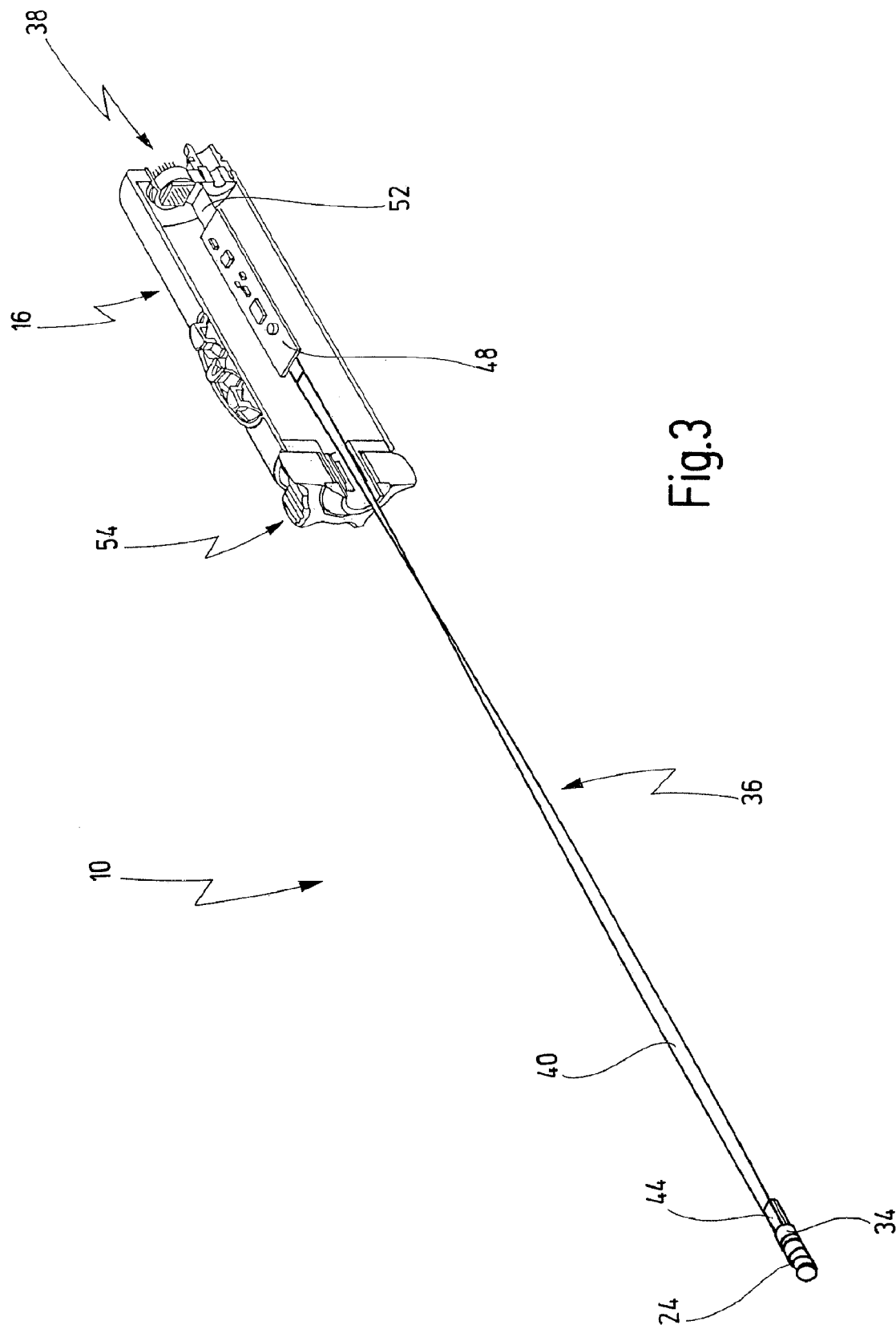
FIG. 3 shows a view of the video endoscope in FIG. 1 comparable to the view in FIG. 1, but in another operating state compared to FIG. 1.
Figure 4:
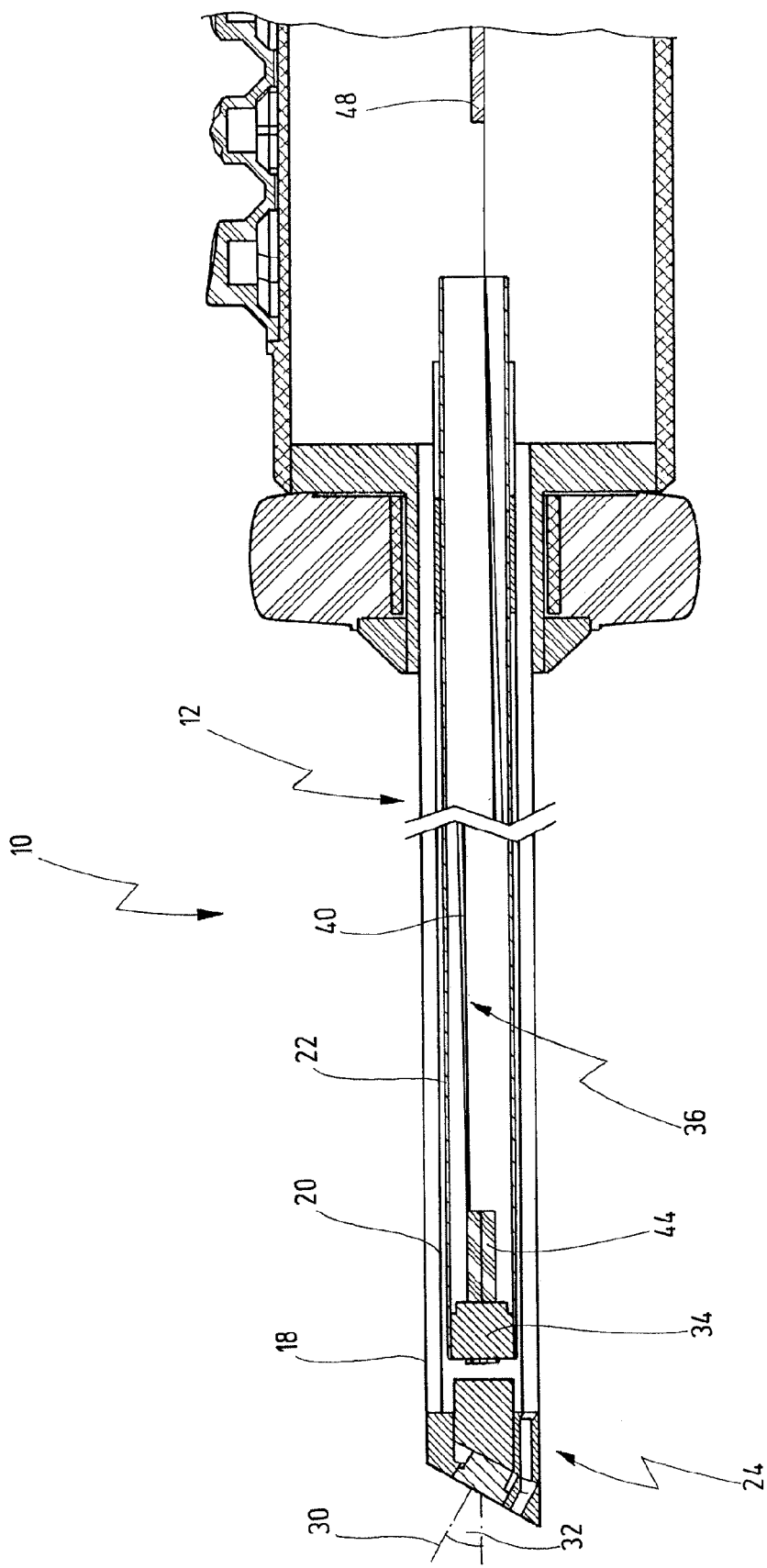
FIG. 4 shows the video endoscope in a view comparable to FIG. 2 and in the operating state shown in FIG. 3.
Figure 5:
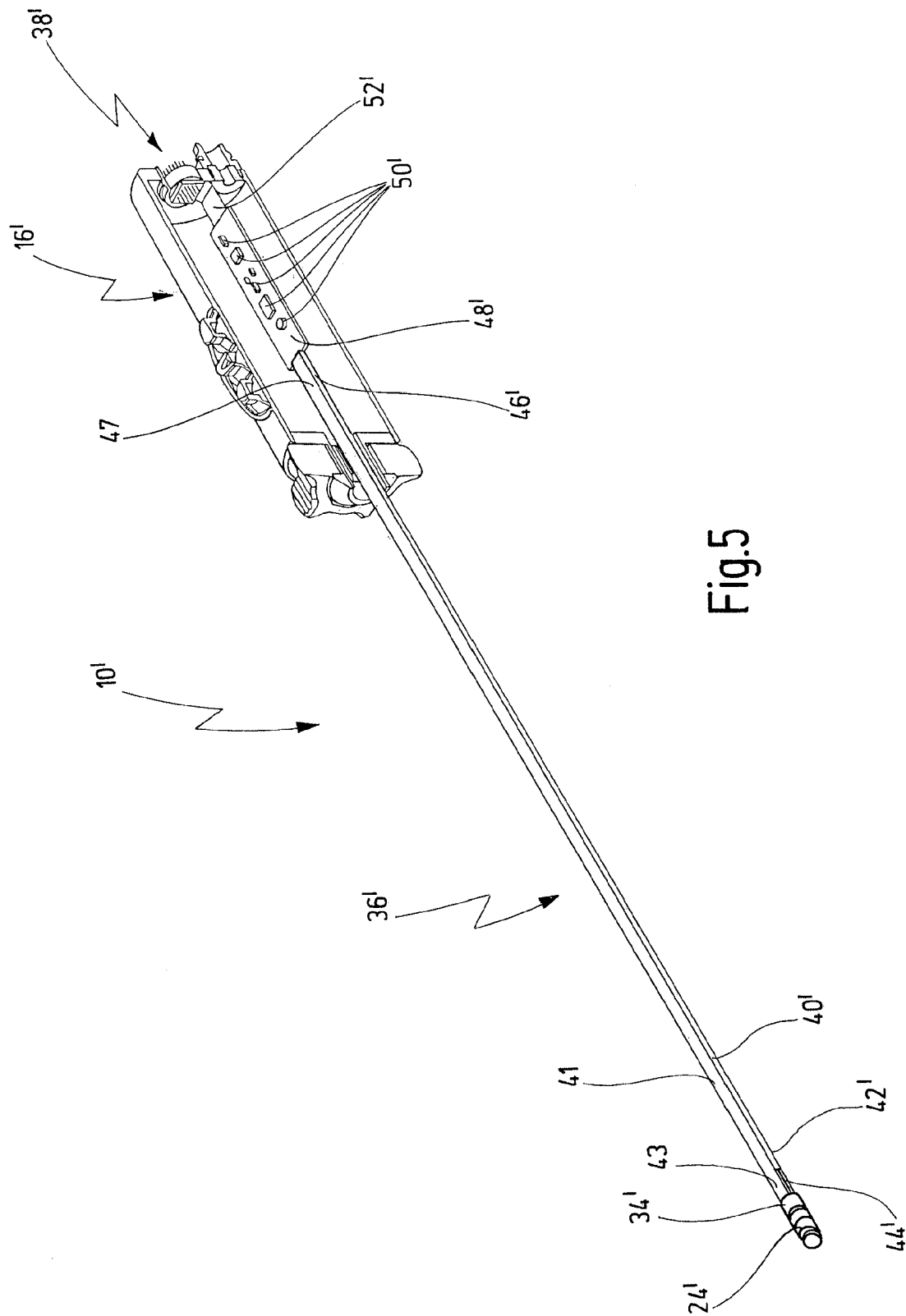
FIG. 5 shows a perspective view of a video endoscope according to another illustrative embodiment, where parts of the video endoscope have been omitted, and where the video endoscope is depicted partially in longitudinal section.

The video endoscope 10 comprises, according to FIGS. 2 and 4, an elongate shaft 12, which has been omitted in FIGS. 1 and 3 for the sake of clarity. The shaft 12 has a longitudinal axis 14. At the proximal end of the shaft 12, the video endoscope 10 has a handpiece 16, to which the shaft 12 is connected.

In the illustrative embodiment shown, the shaft 12 is made up of several tubes pushed one inside another, specifically an outer tube 18, a middle tube 20 arranged therein, and an inner tube 22. The construction of the shaft 12 from a plurality of tubes, in this case the tubes 18, 20 and 22, is optional, and the shaft 12 can also be made tip of one tube, two tubes, or more than three tubes. The inner tube 22 is able to rotate about the longitudinal axis 14 relative to the other two tubes 18, 20.

Arranged at the distal end of the shaft 12 there is a lens 24 which, for example, has two optical elements 26 and 28. The lens 24 is an oblique view lens, i.e. a viewing direction 30 of the lens 24 forms an angle 32 of ≠0° with the longitudinal axis 14 of the shaft 12, and, in the illustrative embodiment shown, the angle 32 is 30°. The lens is connected in a rotationally fixed manner to the middle and outer tubes 18, 20 of the shaft 12.

Arranged in the proximal direction from the lens 24, but still at the distal end of the shaft 12, there is an electronic image pickup 34. In the illustrative embodiment shown, the electronic image pickup 34 is securely connected to the distal end of the inner tube 22.

Further optical elements, for example one or more filters, can be arranged between the lens 24 and the image pickup 34.

The electronic image pickup 34 is designed, for example, in the form of a CCD or CMOS chip.

The lens 24 projects the viewed area of the body onto the image pickup 34. The image pickup 34 converts the received optical signals into electrical signals.

The electronic image pickup 34 is connected, via an electrical connection 36, to an electrical connector piece 38, which is here arranged at the proximal end of the handpiece 16. The electrical connector piece 38 is designed as a plug.

The electrical connection 36 is formed by at least one (in the illustrative embodiment according to FIGS. 1 to 4 by precisely one) flexible, elongate and narrow circuit board 40, which is itself able to twist about its longitudinal direction, which corresponds to the direction of the longitudinal axis 14.

As is shown in the enlarged detail in FIG. 1A, the circuit board 40 carries a plurality of conductor tracks, for example in this case four conductor tracks 40a, 40b on one of its surfaces, which are designed as thin copper lines, for example. On the opposite side, the circuit board 40 can carry further conductor tracks.

A distal end 42 of the circuit board 40 is adjoined in the distal direction by a distal circuit board part 44, which is rigid, or at least stiffer than the flexible circuit board 40. The distal circuit board part 44 serves for contact with the electronic image pickup 34. As will be seen from FIG. 1, the width B of the circuit board 40 and of the distal circuit board part 44 is not greater than the corresponding width of the image pickup 34. As can be seen from FIG. 2, the distal circuit board part 44 is thicker than the circuit board 40, which is made as thin as possible in order to achieve a high degree of flexibility.

The circuit board 40 is in this case constructed in one layer from a planar base material, in particular polyimide, and the conductor tracks 40a to 40b are vapour-deposited, for example, onto the base material.

The thickness of the circuit board 40 is preferably 0.02 to 0.3 mm.

The distal circuit board part 44 carries electrical components, for example an amplifier circuit for (pre)amplification of the electrical video signals generated by the image pickup 34.

The circuit board 40 extends all the way through the shaft 12 and into the handpiece 16, where a proximal end 46 of the circuit board 40 is adjoined by a proximal circuit board part 48.

The proximal circuit board part 48 carries further electrical components 50 for controlling the image pickup 34.

The proximal circuit board part 48 is again stiffer than the circuit board 40 and can in particular also be rigid, thus making it easier to apply the electrical components 50.

The proximal circuit board part 48 carries the electrical connector piece 38 at its proximal end, said electrical connector piece 38 in this case being designed as a plug contact. The electrical connector piece 38 is connected to the proximal circuit board part 48 via a flexible bridge 52.

The circuit board 40, the distal circuit board part 44 and the proximal circuit board part 48 and bridge 52 can all be produced in one piece from the same base material, in which case the different degrees of flexibility between the circuit board 40, the distal circuit board part 44 and the proximal circuit board part 48 can be obtained by suitable strengthening of the base material in the area of the distal circuit board part 44 and of the proximal circuit board part 48.

However, the arrangement of circuit board 40, distal circuit board part 44 and proximal circuit board part 48 can also be designed as a hybrid arrangement, i.e. the distal and proximal circuit board parts 44 and 48 can be produced from one base material, in particular a stiff base material, while the circuit board 40 can be produced from a particularly flexible base material, in particular a polymer, especially polyimide, and the individual circuit board parts are then connected to one another in a suitable way, for example by adhesive bonding. The polymer can also be thermosetting.

The circuit board 40 is preferably in one layer, and the conductor tracks 40*a* to 40*d* are arranged in at most two planes of the circuit board, for example on the two mutually opposite wide sides of the circuit board 40.

However, the circuit board 40 can also have a multi-layer design, preferably constructed from two circuit board layers that are firmly connected to each other. However, to permit the greatest possible flexibility of the circuit board 40, it must be ensured that the thickness of the circuit board 40 is kept as small as possible.

It is also possible for the circuit board 40 to be provided with different degrees of flexibility between its proximal end 46 and its distal end 42, with the flexibility decreasing from the proximal end 46 towards the distal end 42, i.e. the circuit board 40 is stiffer in the area of the distal end 42 than it is in the area of the proximal end 46.

As will be seen from FIG. 2, the distal circuit board part 44 is constructed from two circuit board part layers 44*a* and 44*b*.

The electronic image pickup 34 is also rotatable about the longitudinal axis 14 of the shaft 12 relative to the electrical connector piece 38 and to the lens 24. For this rotation, an adjustment member 54 is provided which acts on the inner tube 22 and turns the latter about the longitudinal axis 14 of the shaft, as a result of which the image pickup 34, which is fixedly connected to the inner tube 22, is likewise rotated about the longitudinal axis 14. By the rotation of the image pickup 34, it is possible for the video picture displayed on the monitor (not shown) to be kept at all times in a desired orientation with respect to top, bottom, right and left, i.e. for the video picture to be positioned in the desired manner. The image pickup 34 is rotatable about the longitudinal axis 14 in both directions of rotation (clockwise and anticlockwise), preferably by 180°.

A rotation of the image pickup 34 relative to the electrical connector piece 38 then causes a twisting of the circuit board 40, as is shown in FIGS. 3 and 4.

This twisting of the circuit board 40 is made possible by the fact that the circuit board 40 is itself designed to be flexible in order to be able to twist. FIG. 3 shows the state in which the image pickup 34 is rotated through 180° about the longitudinal axis 14 relative to the position in FIG. 1. The proximal circuit board part 48 has not twisted, or has not appreciably twisted, whereas the distal circuit board part 44 has twisted through 180° along with the image pickup 34. Because of the narrow width B of the circuit board 40, the conductor tracks 40*a* to 40*d* are not subjected or are subjected only minimally to compression and extension, as a result of which there is no risk of the conductor tracks 40*a* to 40*d* breaking, even in long-term use of the video endoscope 10.

Between the outer tube 18 and the middle tube 20, the video endoscope 10 has a channel 56 in which optical fibres extend for the illuminating light, a connector piece 58 for a fibre optic cable (not shown) being provided at the proximal end, and the light emerging from a light exit port 60 at the distal end of the shaft 12.

FIGS. 5 to 8 show another illustrative embodiment of a video endoscope 10' in which parts that are identical or comparable to those in the video endoscope 10 are provided with the same reference numbers, with an added prime sign. Only the differences from the video endoscope 10 are described below.

In the video endoscope 10', the electrical connection 36' between the image pickup 34' and the electrical connector piece 38' is formed by two circuit boards 40' and 41, which are arranged lying one over the other in the shaft 12' along the longitudinal axis 14'.

The distal ends 42', 43' of the circuit boards 40' and 41 are once again adjoined by the distal circuit board part 44'.

By using two circuit boards 40' and 41, the number of conductor tracks for the electrical connection between the image pickup 34' and the connector piece 38' can be increased without widening the individual circuit boards 40' and 41', and without the thickness and therefore the stiffness of the circuit boards 40' and 41 being increased. Like the circuit board 40', the circuit board 41 is also flexible and able to twist about its longitudinal direction.

Figure 6:
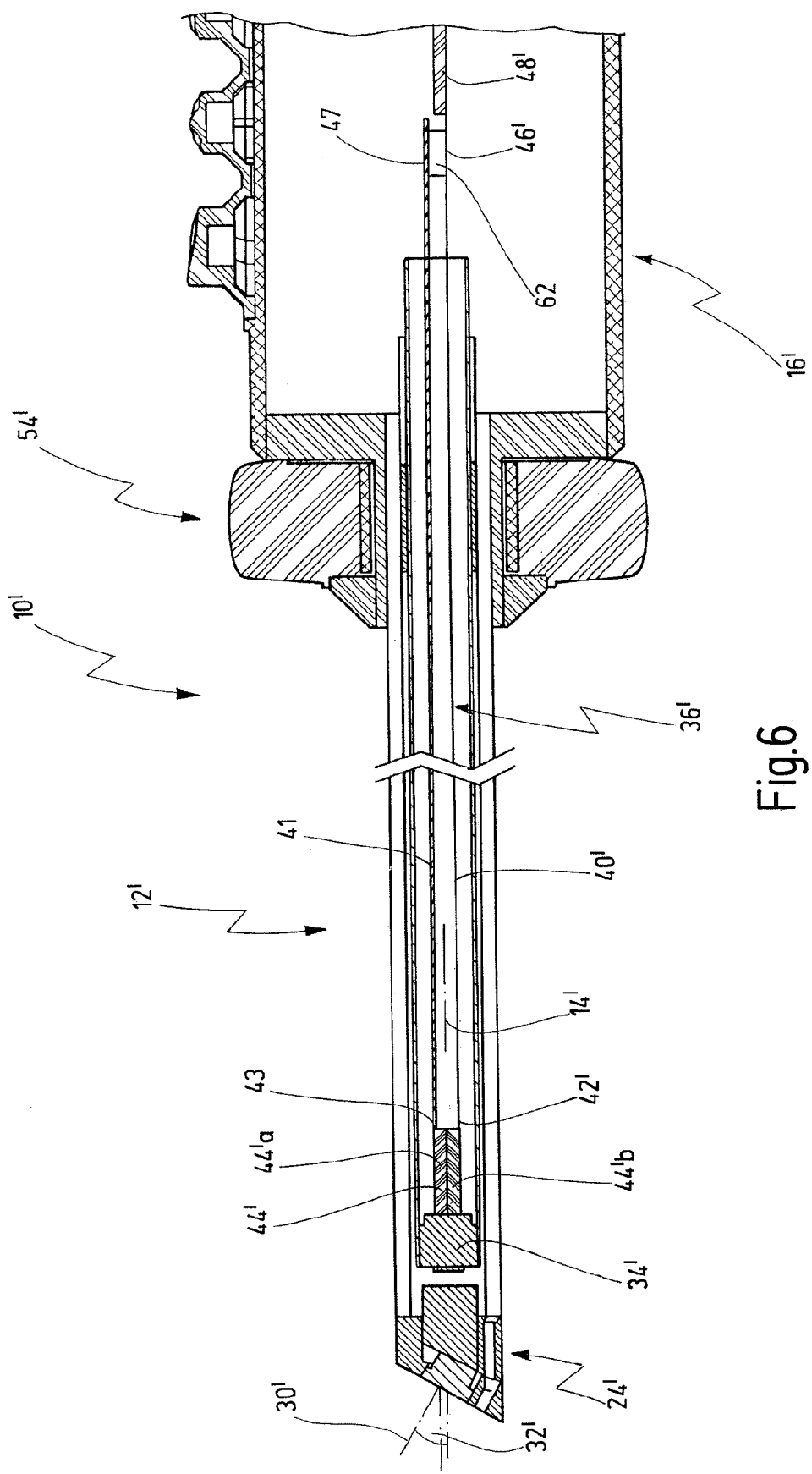
FIG. 6 shows a cutaway view of the video endoscope in FIG. 5, on an enlarged scale and in longitudinal section.

As will be seen from FIG. 6, the circuit board 41 and the circuit board 40' are at a distance from each other and therefore movable relative to each other, as a result of which the overall flexibility of the two circuit boards 40' and 41 is not reduced, or is not appreciably reduced, by comparison with just one circuit board.

At their proximal ends 46' and 47, the circuit boards 41 and 40' are connected to each other via a flexible bridge 62, which bridge 62 also forms an electrical connection between the circuit boards 40' and 41. Thus, the proximal circuit board part 48' need only be electrically connected to the circuit board 40'.

Before installation of the circuit boards 40' and 41, they are preferably folded out from each other (cf. also FIG. 9) such that they lie in one plane. The circuit board part layer 44'*a* is connected to the circuit board 41, and the circuit board part layer 44'*b* of the distal circuit board part 44' is connected to the circuit board 40'. To insert the circuit boards 40' and 41, they are then bent via the bridge 62 into an arrangement in which they lie one over the other, as is shown in FIG. 6, where the circuit board parts 44'*a* and 44'*b* are moved relative to each other upon insertion such that they can be pushed more easily through the shaft (inner tube 22).

Figure 7:
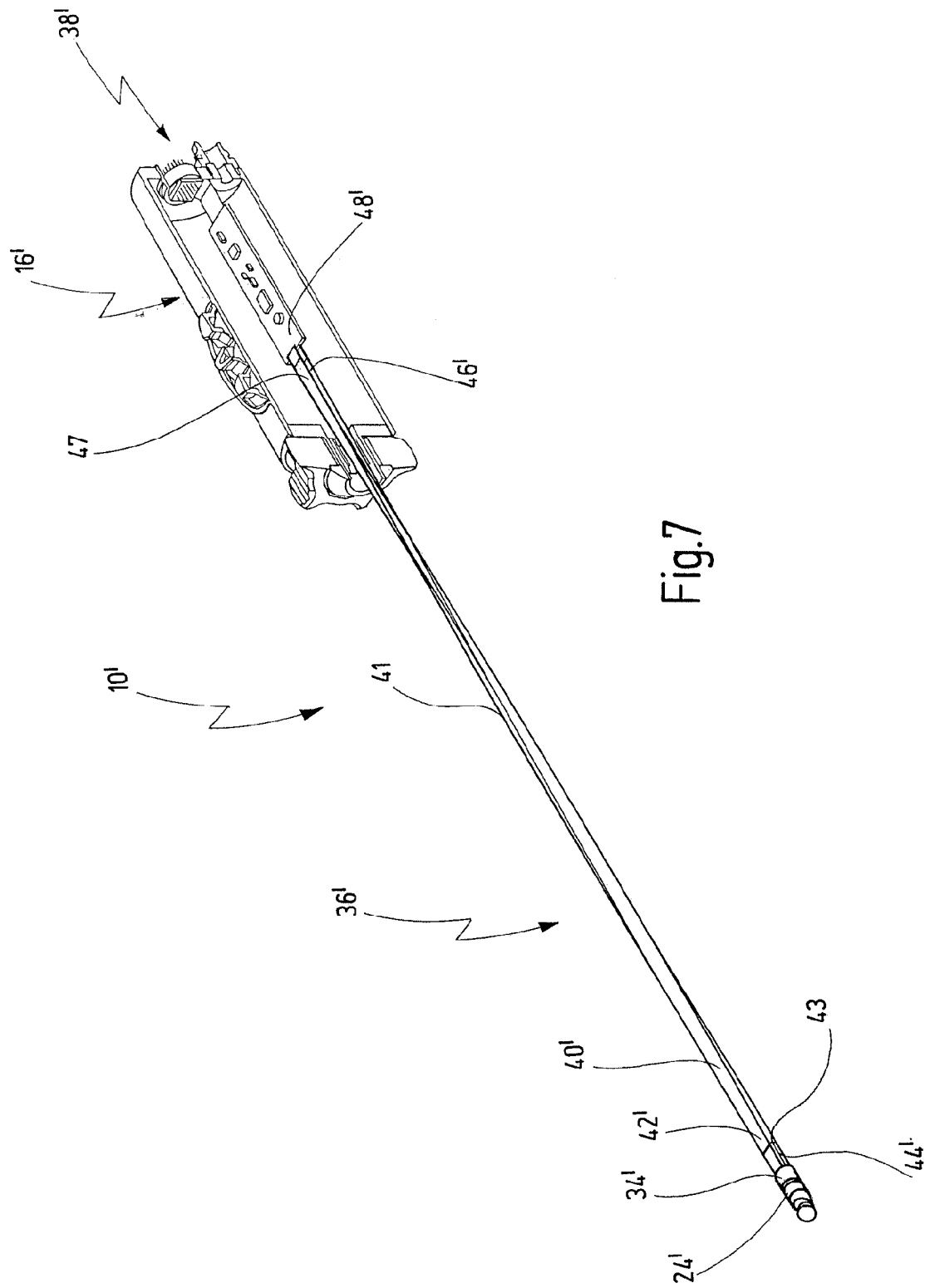
FIG. 7 shows the video endoscope from FIG. 5 in a view comparable to FIG. 5, but in another operating state compared to FIG. 5.
Figure 8:
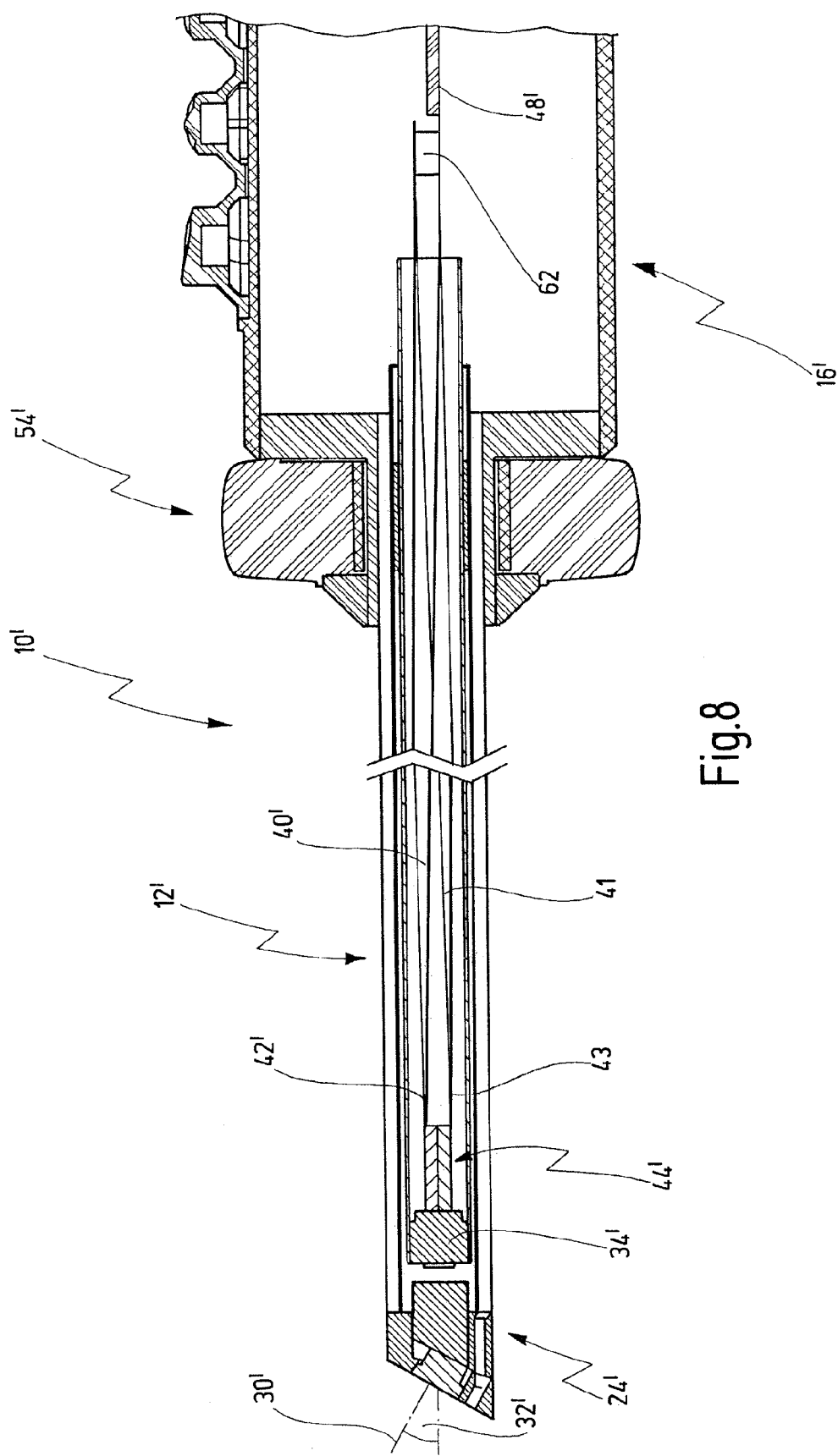
FIG. 8 shows the video endoscope from FIG. 5 in a view comparable to FIG. 6, and in the operating state of the video endoscope according to FIG. 7.

FIG. 7 shows the video endoscope 10' in a state in which the image pickup 34' has been rotated through 180° from its position in FIG. 6. As will be seen from FIGS. 7 and 8, the arrangement of the circuit boards 40' and 41 lying one over the other and at a distance from each other ensures that they can move relative to each other and can each twist.

In the case where the electrical connection 36' is formed by means of two circuit boards 40' and 41, these can be produced in one piece together with the circuit board parts 44' and 48' and the bridge 62 from the same planar base material, or they can be formed in a hybrid configuration from different base materials used for the circuit board parts 44' and 48' and the circuit boards 40', 41.

FIG. 9 shows another variant of an electrical connection 36" which can be used in the video endoscope 10 or the video endoscope 10' instead of the electrical connections 36 and 36'.

Here, parts that are comparable or identical to the illustrative embodiments according to FIGS. 1 to 4 and FIGS. 5 to 8, respectively, have once again been provided with the same reference numbers, with an added double prime sign.

The electrical connection 36" here has two circuit boards 40" and 41", the circuit board 40" having a distal circuit board part 44b" at its distal end, and the circuit board 41" having a distal circuit board part 44a" at its distal end. The arrangement to this extent corresponds to the embodiment in FIGS. 5 to 8, with the circuit boards 40" and 41" still being arranged lying next to each other. At their proximal end, the circuit boards 40" and 41" are connected to each other via the flexible bridge 62". In the installed state in the video endoscope 10 or 10', the circuit board 41" with its distal circuit board part 44a" is folded through 180° about a mirror axis 64 and onto the circuit board 40", such that the resulting arrangement corresponds to the arrangement of the circuit boards 40' and 41 according to FIGS. 5 to 8.

The electrical connection 36" differs from the previous electrical connections 36 and 36' in that the proximal circuit board part 48" is constructed in two parts, specifically a first circuit board part 48a" and a second circuit board part 48b". The circuit board parts 48a" and 48b" are connected via a flexible bridge 49, which connects the circuit board parts 48a" and 48b" not just mechanically, but also electrically.

The electrical connector piece 38" is provided on the circuit board part 48a" via the flexible bridge 52".

In the installed state of the electrical connection 36" in the video endoscope 10 or the video endoscope 10', the circuit board parts 48a" and 48b" are folded onto each other about an axis 66, i.e. they then lie one over the other in the handpiece 16 or 16'. Both circuit board parts 48a" and 48b" carry the electrical components 50a" and 50b".

What is claimed is:

1. A video endoscope, comprising:
   an elongate shaft having a distal end, a proximal end and a longitudinal axis between the distal end and the proximal end;
   a handpiece arranged at the proximal end of the shaft;
   a lens arranged at the distal end of the shaft;
   an image pickup arranged at the distal end of the shaft proximally from the lens;
   an electrical connector piece arranged on the handpiece;
   the image pickup and the electrical connector piece being able to rotate relative to one another about the longitudinal axis of the shaft; and
   at least one flexible, elongate and narrow circuit board for electrically connecting the image pickup with the electrical connector piece, the at least one circuit board extending along the shaft and having a longitudinal direction, the at least one circuit board being able to twist about the longitudinal direction and having at least one conductor track.

2. The video endoscope of claim 1, wherein the at least one circuit board has a plurality of conductor tracks that are arranged next to one another and at most in two planes of the at least one circuit board.

3. The video endoscope of claim 1, wherein the at least one circuit board is a first circuit board, further comprising a second flexible, elongate and narrow circuit board having a second longitudinal direction, the second circuit board being able to twist about the second longitudinal direction and having at least one conductor track.

4. The video endoscope of claim 3, wherein the first and second circuit boards are arranged lying one over the other in the shaft and are movable relative to each other.

5. The video endoscope of claim 3, wherein the first circuit board has a first proximal end, the second circuit board has a second proximal end, the first and second circuit boards are connected to each other in an area of the first and second proximal ends via a flexible bridge.

6. The video endoscope of claim 3, wherein the first circuit board has a first proximal end, the second circuit board has a second proximal end, the first and second circuit boards are connected to each other in an area of the first and second proximal ends via a flexible bridge, and wherein the first and second circuit boards and the bridge are produced in one piece from a planar base material.

7. The video endoscope of claim 1, wherein the at least one circuit board has a proximal end, and is adjoined at the proximal end by at least one proximal rigid circuit board part, which carries electrical components.

8. The video endoscope of claim 7, wherein the proximal circuit board part is a first proximal circuit board part and is connected by a flexible bridge to a second proximal rigid circuit board part, which carries electrical components.

9. The video endoscope of claim 8, wherein the first and second proximal circuit board parts are arranged lying one over the other in the handpiece.

10. The video endoscope of claim 7, wherein the at least one circuit board part comprises the electrical connector piece.

11. The video endoscope of claim 7, wherein the at least one circuit board and the at least one proximal circuit board part are constructed in one piece from a planar base material.

12. The video endoscope of claim 7, wherein the at least one circuit board and the at least one proximal circuit board part are produced from different base materials.

13. The video endoscope of claim 7, wherein the at least one circuit board and the at least one proximal circuit board part are produced from the same base material, but have different degrees of flexibility.

14. The video endoscope of claim 1, wherein the at least one circuit board has a distal end, and, arranged at the distal end, a distal rigid circuit board part for contact with the image pickup.

15. The video endoscope of claim 14, wherein the at least one circuit board and the at least one distal circuit board part are produced in one piece from a planar base material.

16. The video endoscope of claim 14, wherein the at least one circuit board and the at least one distal circuit board part are produced from different base materials.

17. The video endoscope of claim 14, wherein the at least one circuit board and the at least one distal circuit board part are produced from the same base material, but have different degrees of flexibility.

18. The video endoscope of claim 1, wherein the at least one circuit board has a distal end and a proximal end, wherein a flexibility of the at least one circuit board decreases from the proximal end to the distal end.

19. The video endoscope of claim 1, wherein the at least one circuit board has a width which is at most as great as a width of the image pickup.

20. The video endoscope of claim 1, wherein the at least one circuit board is produced in one piece from a planar base material.

21. The video endoscope of claim 1, wherein the at least one circuit board is constructed from a plurality of circuit board sections that have different degrees of flexibility.

22. The video endoscope of claim 1, wherein the at least one circuit board is constructed, at least in an area in which the at least one circuit board is flexible, from a plurality of circuit board layers.

23. The video endoscope of claim 22, wherein the at least one circuit board is constructed from two circuit board layers.

* * * * *